US008119813B2

(12) United States Patent
Bigot et al.

(10) Patent No.: US 8,119,813 B2

(45) Date of Patent: Feb. 21, 2012

(54) **METHOD FOR PREPARING ENANTIOMERICALLY ENRICHED *N*-CARBOXYANHYDRIDE**

(75) Inventors: Antony Bigot, Paris (FR); Maxime Lampilas, Paris (FR)

(73) Assignee: sanofi-aventis, Paris (FR)

( * ) Notice: Subject to any disclaimer, the term of this patent is extended or adjusted under 35 U.S.C. 154(b) by 280 days.

(21) Appl. No.: 12/617,398

(22) Filed: Nov. 12, 2009

(65) Prior Publication Data

US 2010/0113797 A1 May 6, 2010

Related U.S. Application Data

(63) Continuation of application No. PCT/FR2008/000703, filed on May 22, 2008.

(30) Foreign Application Priority Data

May 25, 2007 (FR) ..................................... 07 03702

(51) Int. Cl.
*C07D 263/04* (2006.01)
*C07C 271/18* (2006.01)

(52) U.S. Cl. ....................................... 548/225; 560/160

(58) Field of Classification Search ........................ None
See application file for complete search history.

(56) References Cited

OTHER PUBLICATIONS

Hanby et al., Synthetic Polypeptides, Part I. J. Chem. Soc. , 1950, pp. 3009-3013.*

Akssira et al, A Convenient One-Pot Preparation of N-Methyl-N-Carboxyaminoacid Anhydrides (alpha-Methyl-NCAs), J Mar Chim Heterocycl; 2002 (1) 1 pp. 44-47.

Akssira et al, New Routes to 1,4-Benzodiazepin-2,5-diones, Tetrahedron; 1994 (50) 30 pp. 9051-9060.

Coste et al, Coupling N-Methylated Amino Acids Using PyBroP(1) and PyCloP Halogenophosphonium Salts: Mechanism and Fields of Application, J. Org. Chem.; 1994 (59) pp. 2437-2446.

Hanby et al, Synthetic Polypeptides. Part I., J Chemical Soc; 1950 pp. 3009-3013.

Nielsen et al, Combinatorial Solid-Phase Synthesis of Balanol Analogues, Tetrahedron Letters; 1996 (37) 46 pp. 8439-8442.

Savrda et al, Activation of N,N-bis(alkoxycarbonyl) Amino Acids, Synthesis of N-Alkoxycarbonyl Amino Acid N-Carboxyanhydrides and N,N-Dialkoxycarbonyl Amino Acid Fluorides, and the behavior of these Amino Acid Derivatives, Tetrahedron; 1994 (50) 18 pp. 5309-5322.

Wessely, Untersuchungen uber alpha-Amino-N-Carbonsaureanhydride. I., Hoppe-Seyler's Zeitschrift Fuer Physiologische Chemie; 1925 (146) pp. 72-90.

Zhu et al, Total Synthesis of Microsclerodermin E, Angew. Chem. Int. Ed.; 2003 (42) pp. 5348-5351.

* cited by examiner

*Primary Examiner* — Rebecca Anderson
*Assistant Examiner* — Alicia L Otton
(74) *Attorney, Agent, or Firm* — Brian R. Morrill

(57) ABSTRACT

This disclosure relates to methods for preparing an enantiomerically enriched N-carboxyanhydride of an amino alpha acid of the formula (IIIa) or (IIIb):

(IIIa)

R1, R2, N, O, O, O (IIIb)

R1, R2, N, O, O, O from a compound of the formula (IIa) or (IIb), respectively:

(IIa)

R1, R2, N, O, R3, O, O, O, H (IIb)

R1, R2, N, O, R3, O, O, O, H wherein R1, R2, and R3 are as defined in the disclosure.

22 Claims, No Drawings

METHOD FOR PREPARING ENANTIOMERICALLY ENRICHED *N*-CARBOXYANHYDRIDE

This application is a continuation of International Application No. PCT/FR2008/000703, filed May 22, 2008, which is incorporated herein by reference in its entirety; which claims the benefit of priority of French Patent Application No. 0703702, filed May 25, 2007.

The present application relates to a method for preparing an enantiomerically enriched α-amino acid N-carboxyanhydride, more particularly (L)- or (D)-N-methylalanine carboxyanhydride. The application also relates to a chemical intermediate which is used in the preparation of (L)- or (D)-N-methylalanine carboxyanhydride.

TECHNICAL FIELD AND TECHNICAL PROBLEM

Amino acid N-carboxyanhydrides are acylating agents that have the advantage of not forming troublesome by-products in the acylation reactions. When they are enantiomerically enriched, they furthermore make it possible to introduce a chiral carbon. These are therefore chemical compounds that are useful in organic syntheses, in particular in the case of syntheses of pharmaceutical compounds which are often syntheses having several reaction steps. However, it is necessary that these compounds have sufficient purity, in particular enantiomeric purity. The industrial preparation method must additionally be simple and have a good overall yield.

The Applicant has developed a simple method of preparing α-amino acid N-carboxyanhydride having a good overall yield and that makes it possible to attain a pure and enantiomerically enriched product. This method applies more particularly to (L)- or (D)-N-methylalanine carboxyanhydride.

In Tetrahedron 1994, 50, No. 18, 5309-5322, the preparation of N-carboxyanhydrides protected on the nitrogen atom by RO—C(═O)— from N,N-bis(alkoxycarbonyl)amino acids and the Vilsmeier-Haack reagent $SOCl_2$/DMF is described.

In the article "Untersuchungen über Alpha-amino-N-carbonsäureanhydride. I" from Zeitschrift für Physiologische Chemie", Walter de Bruyter, Berlin 1925, 46, 72-90, the preparation of N-carboxyanhydrides is described, but without any purification step.

In Angew. Chem. Int. Ed. 2003, 42, 5348-5351, the preparation of N-carboxyanhydrides protected on the nitrogen atom by RO—C(═O)— is described in Scheme 3 referring to Tetrahedron Letters 1996, 37, 8439, but no purification step is described.

In J. Org. Chem. 1994, 59, 2437-2446, the preparation of N-carboxyanhydrides is described but using another chemical reaction.

In Tetrahedron 1994, 50, 30, 9051-9060, the preparation of N-carboxyanhydrides from amino acids protected by tBuO-C(═O)— (BOC) and $PCl_3$ is described. The use of $PCl_3$ leads to the formation of phosphorus-containing by-products which remain combined with the N-carboxyanhydride and which it is necessary to remove by a step of washing with an industrially unacceptable perchlorinated solvent ($CCl_4$).

In Journal of Chemical Society 1950, 3009-3013, the preparation of N-carboxyanhydrides is carried out starting from a mixture of the two amino acids (D and L) protected by MeO—C(═O)— and $SOCl_2$ and not starting from the D or else L amino acid. Furthermore, the final product is obtained after a precipitation step, a recrystallization step and a sublimation step. The calculated yield, by weight, is only 39%.

In J. Mar. Chim. Heterocycl. 2002, 1, 44-47, the preparation of N-carboxyanhydrides is carried out starting from a protected amino acid and $POCl_3$.

None of these documents describes or suggests the method of the invention.

DESCRIPTION OF THE INVENTION

Definitions Used

- alkyl group: a linear or branched, saturated aliphatic hydrocarbon-based group. As examples, mention may be made of methyl, ethyl, propyl, isopropyl, butyl, isobutyl and tert-butyl groups. It is preferably a ($C_1$-$C_4$) group;
- alkenyl group: an alkyl group comprising a C═C double bond;
- cycloalkyl group: a cyclic alkyl group comprising between 3 and 8 carbon atoms, all the carbon atoms being incorporated in the cyclic structure. As examples, mention may be made of cyclopropyl, cyclobutyl, cyclopentyl and cyclohexyl groups; and
- aryl group: an aromatic group comprising from 6 to 10 ring members, for example a phenyl group.

The present invention relates to a method for preparing an enantiomerically enriched α-amino acid N-carboxyanhydride of formula (IIIa):

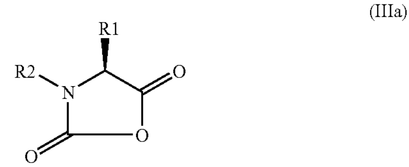

from the compound of formula (IIa):

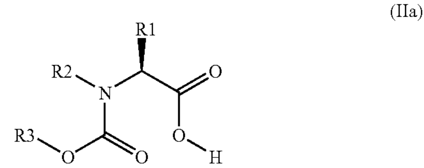

in which formulae:

- R1 and R2 denote, independently of one another, an alkyl (e.g. methyl, ethyl, isopropyl), alkenyl (e.g. allyl), cycloalkyl, alkylcycloalkyl (e.g. —$CH_2$-cyclohexyl), alkylaryl (e.g. benzyl) or aryl group;
- R3 denotes an alkyl (e.g. methyl, ethyl, tert-butyl) or alkylaryl (e.g. benzyl) group;

comprising the following steps:

(i) bringing the compound of formula (IIa) (or (IIb) respectively) into contact with $SOCl_2$ in a solvent;

(ii) precipitating the N-carboxyanhydride formed in step (i) using a non-solvent; and (iii) recovering the N-carboxyanhydride.

This method does not comprise any recrystallization step nor sublimation step of the N-carboxyanhydride.

This method applies in a similar manner to the compound (IIIb) from the compound (IIb):

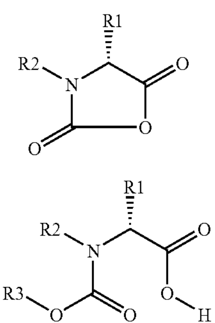

Preferably, R3 denotes a methyl or ethyl group, more preferably still a methyl group, since, at the end of step (i), a light compound (R3Cl) is then formed which may be easily removed.

Preferably, R1 and R2 denote, independently of one another, a methyl or ethyl group. More preferably, R1 and R2 both denote a methyl group and the N-carboxyanhydride of formula (A) (or (B)) below is obtained:

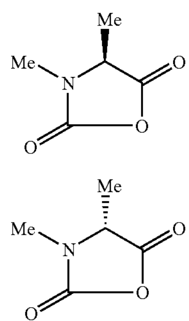

(A) is (L)-N-methylalanine N-carboxyanhydride. Preferably, use is made of the compound (IIa) of formula:

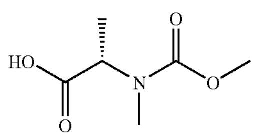

which is the methyl carbamate of (L)-N-methylalanine.

(B) is (D)-N-methylalanine N-carboxyanhydride. Preferably, use is made of the compound (IIb) which is the carbamate of (D)-N-methylalanine:

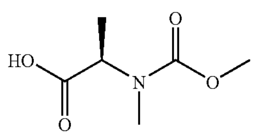

Step (i)

The solvent from step (i) may be a chlorinated solvent such as dichloromethane, an alkyl or aryl ether such as, for example, tetrahydrofuran, 2-methyltetrahydrofuran or 1,4-dioxane, an aromatic solvent such as, for example, toluene, a xylene or trifluoromethylbenzene, a ketone such as, for example, acetone, methyl isobutyl ketone or methyl ethyl ketone. It is also possible to use a mixture of two or more of these solvents.

Use is generally made of between 1 and 3 equivalent(s) of $SOCl_2$ relative to the compound (IIa) (or (IIb)).

The reaction is carried out at a temperature between −10 and 50° C., preferably between 0 and 30° C., more preferably still between 20 and 30° C. The reaction time is generally between 30 and 60 min.

Step (ii)

The precipitation of the N-carboxyanhydride formed in step (i) is carried out using a non-solvent. Use is advantageously made of a liquid alkane (e.g. n-heptane or octane) or else an oil cut (e.g. petroleum ether). The N-carboxyanhydride may first be concentrated by eliminating some of the solvent from the reaction from step (i).

It is possible to use, as a solvent/non-solvent pair, a chlorinated solvent and a liquid alkane or oil cut, especially the dichloromethane/n-heptane pair described in Example 2.

Step (iii)

The N-carboxyanhydride may be recovered simply by filtration/drying. This is one of the advantages of the method of the invention, namely not requiring a recrystallization or sublimation step to obtain sufficient purity and a good yield. The advantage of using a liquid alkane in step (ii) is in being able to easily dry the N-carboxyanhydride.

Preparation of the Compound of Formula (IIa) or (IIb)

The compound of formula (IIa) (or (IIb)) may be prepared according to the following reaction (optionally in the course of a step preceding step (i)):

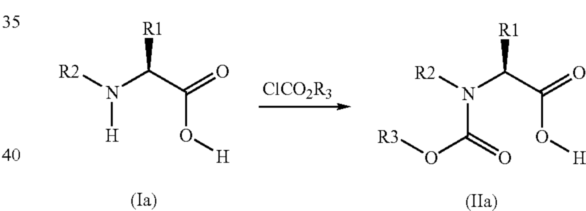

(or else respectively according to:

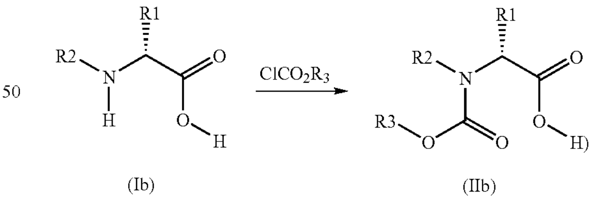

in the presence of a base. The base may be, for example, a carbonate, a bicarbonate or a hydroxide of an alkali metal. A preferred base is NaOH.

This reaction may be carried out in a solvent which may be, for example, water or one of the solvents cited previously. The reaction is carried out at a temperature between 0 and 5° C. The reaction time is generally between 5 and 6 hours. Preferably, a $ClCO_2R3$/(IIa) (or (IIb)) molar ratio>1.9 is used. Also preferably, a base/(IIa) (or (IIb)) molar ratio>2 is used.

The method of the present invention makes it possible to obtain (whether or not the method includes the reaction preceding step (i)) an N-carboxyanhydride in a simple manner, with a good yield (>the yield disclosed in Journal of the Chemical Society, 1950) and high purity. In particular, it does not require any recrystallization nor sublimation step. The cyclization in step (i) preserves the integrity of the asymmetric centre and makes it possible to obtain an enantiomerically enriched product (no epimerization).

EXAMPLES

A person skilled in the art could advantageously take inspiration from the conditions disclosed in the following two examples.

Ex. 1

Preparation of (S)-2-(methoxycarbonylmethylamino)propionic acid (C)

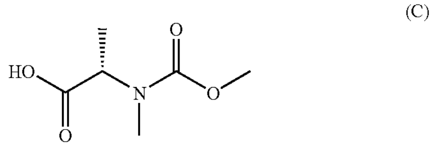

A 250 ml two-necked flask, under a nitrogen atmosphere, was successively charged with: 10 g (97 mmol) of (L)-N-methylalanine, then 200 ml of a 1 M aqueous solution of NaOH (200 mmol, 2.06 eq.). The white suspension thus obtained was stirred until it had completely dissolved (around 30 minutes). This solution was cooled to around 3° C. using a water/ice bath and, with vigorous stirring (around 750 rpm), 15 ml of methyl chloroformate (192 mmol, 1.98 eq.) were added over around 30 minutes using a 50 ml dropping funnel. The two-phase medium thus obtained was stirred at 3° C.

After 6 hours, the temperature of the reaction medium was raised to around 20° C. by removing the ice/water bath, and the pH of the reaction medium was brought to around 1 (measured with pH paper) using 37% aqueous HCl. This aqueous phase was then extracted with 3 times 50 ml of AcOEt. The organic phases were combined, washed with 50 ml of demineralized water, then dried over around 10 g of anhydrous $MgSO_4$. The medium was filtered through sintered glass, then the filtrate was concentrated to dryness under vacuum (temperature of the bath at around 35° C., vacuum of around 40 mbar). Thus, 13.4 g (86%) of product were obtained in the form of a colourless viscous oil.

Structural analyses: LC-MS-DAD-ELSD: 160(−)=(M−H)(−), 162(+)=(M+H)(+); $^1$H NMR (DMSO-$d_6$ at 400 MHz): for this batch, a 60-40% mixture of conformational isomers was observed, with: 1.31 (d, J=7.5 Hz, 3H); 2.78 (s, 3H); 3.58 (s, 1.2H); 3.60 (s, 1.8H); 4.50 (q, J=7.5 Hz, 0.4H); 4.58 (q, J=7.5 Hz, 0.6H); 10.7 (broad m, 1H).

Analysis by gas chromatography on a chiral column made it possible to show that the enantiomeric excess of the N-methylalanine methyl carbamate was >99%. The conditions for the chromatographic analysis are given below: RT-Gammadex column (30 m/0.25 mm/0.25 μm); isotherm at 120° C. (3 min), then 5° C./min to 180° C., isotherm at 180° C. (3 min); injection split 1:25; helium carrier gas at 1.8 ml/min; FID detection; solution at a concentration of 2 mg/ml in $CH_2Cl_2$, esterification with 0.2 M TMSH. Under these conditions, the (L)-N-methylalanine methyl carbamate had a retention time rt=8.8 min. The other enantiomer, (D)-N-methylalanine methyl carbamate, had a retention time rt=8.5 min.

Ex. 2

Preparation of (S)-3,4-dimethyl-1,3-oxazolidine-2,5-dione 1 g (6.2 mmol) of the product obtained previously was dissolved in 3 ml of $CH_2Cl_2$, stirred for 5 minutes at around 20° C., then treated with $SOCl_2$ (500 μl, 1.1 eq.). The reaction medium was then heated at around 30° C., and the heating was maintained for around 30 min. The reaction medium was then concentrated to around 1.5 volumes, and, still with stirring, 10 ml of n-heptane were added. The white mass thus obtained was then cooled to around −20° C., and stirred for 1 hour at this temperature. The suspension was then filtered through sintered glass, the solid was washed with 3 times 3 ml of n-heptane. After drying in air for 2 hours, the product (700 mg, 87.4%) was obtained in the form of white needles.

Structural analyses: $^1$H NMR (DMSO-$d_6$ at 400 MHz): 1.39 (d, J=7.5 Hz, 3H); 2.83 (s, 3H); 4.40 (q, J=7.5 Hz, 1H).

Analysis by gas chromatography on a chiral column made it possible to show that the enantiomeric excess of (S)-3,4-dimethyl-1,3-oxazolidine-2,5-dione) was >99%, and that no epimerization took place under the cyclization conditions. Gas chromatography conditions: RT-Gammadex column (30 m/0.25 mm/0.25 μm); initial temperature 180° C., then 5° C./min to 220° C., isotherm at 180° C. for 5 min; injection split 1:25; helium carrier gas at 1.8 ml/min; FID detection; solution at a concentration of 2 mg/ml in $CH_2Cl_2$. Under these conditions, the (S)-3,4-dimethyl-1,3-oxazolidine-2,5-dione had a retention time rt=8.4 min. The other enantiomer, (R)-3,4-dimethyl-1,3-oxazolidine-2,5-dione, had a retention time rt=8.7 min.

The overall yield calculated from the initial (L)-N-methylalanine is therefore 86%×87.4%, i.e. 75%. This yield is greater than that obtained in the Journal of the Chemical Society, 1950.

What is claimed is:

1. A method for preparing an enantiomerically enriched α-amino acid N-carboxyanhydride of formula (IIIa) or (IIIb):

(IIIa)

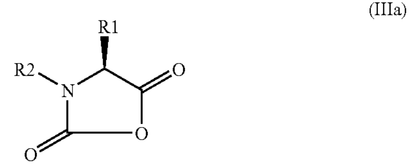

(IIIb)

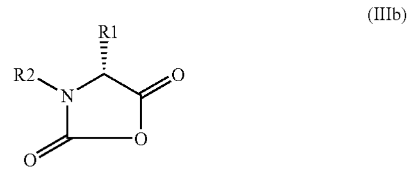

from the compound of formula (IIa) or (IIb) respectively:

(IIa)

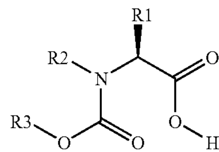

(IIb)

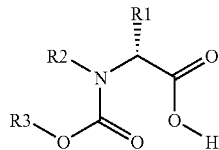

wherein in the formulae:

R1 and R2 denote, independently of one another, an alkyl, alkenyl, cycloalkyl, alkylcycloalkyl, alkylaryl or aryl group; and R3 denotes an alkyl or alkylaryl group;

comprising the following steps:

(i) bringing the compound of formula (IIa) or (IIb) respectively into contact with $SOCl_2$ in a solvent;

(ii) precipitating the N-carboxyanhydride formed in step (i) using a non-solvent; and (iii) recovering the N-carboxyanhydride, and not comprising any recrystallization step, nor a sublimation step of the N-carboxyanhydride.

2. The method according to claim 1, wherein R3 denotes a methyl or ethyl group.

3. The method according to claim 1, wherein R1 and R2 denote, independently of one another, a methyl or ethyl group.

4. The method according to claim 2, wherein R1 and R2 denote, independently of one another, a methyl or ethyl group.

5. The method according to claim 1, wherein R1, R2 and R3 denote a methyl group.

6. The method according to claim 1, wherein the compound of formula (IIa) is prepared according to the following reaction:

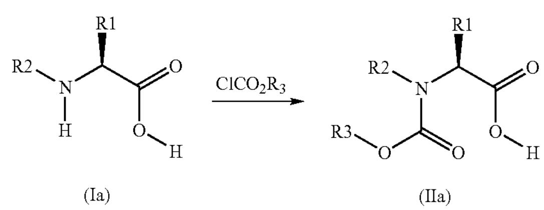

in the presence of a base.

7. The method according to claim 1, wherein the compound of formula (IIb) is prepared according to the following reaction:

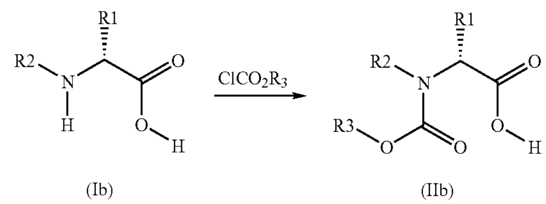

in the presence of a base.

8. The method according to claim 6, in which the reaction constitutes a step preceding step (i).

9. The method according to claim 7, in which the reaction constitutes a step preceding step (i).

10. A method of preparing enantiomerically enriched N-carboxyanhydride of formula (A) or (B):

(A)

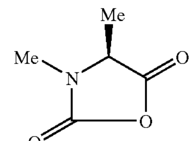

(B)

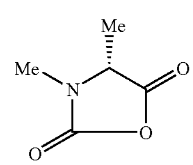

comprising the following steps:

(i) bringing the compound of formula (C)

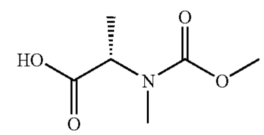

or respectively (D)

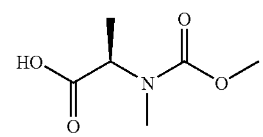

into contact with $SOCl_2$ in a solvent;

(ii) precipitating the N-carboxyanhydride formed in step (i) using a non-solvent; and (iii) recovering the N-carboxyanhydride;

and not comprising any recrystallization step, nor a sublimation step of the N-carboxyanhydride.

11. The method according to claim 1, wherein the reaction from step (i) is carried out at a temperature between −10 and 50° C.

12. The method according to claim 10, wherein the reaction from step (i) is carried out at a temperature between −10 and 50° C.

13. The method according to claim 1, wherein the reaction from step (i) is carried out with 1 to 3 equivalent(s) of $SOCl_2$ relative to the compound (IIa) or (IIb) respectively.

14. The method according to claim 10, wherein the reaction from step (i) is carried out with 1 to 3 equivalent(s) of $SOCl_2$ relative to the compound (C) or (D) respectively.

15. The method according to claim 1, wherein the non-solvent from step (ii) is a liquid alkane or an oil cut.

16. The method according to claim 10, wherein the non-solvent from step (ii) is a liquid alkane or an oil cut.

17. The method according to claim 1, wherein the solvent is a chlorinated solvent and the non-solvent is a liquid alkane or oil cut.

18. The method according to claim 1, wherein the solvent is dichloromethane and the non-solvent is n-heptane.

19. The method according to claim 10, wherein the solvent is dichloromethane and the non-solvent is n-heptane.

20. The method according to claim 1, wherein the recovery of the N-carboxyanhydride from step (iii) is a filtration/drying operation.

21. The method according to claim 10, wherein the recovery of the N-carboxyanhydride from step (iii) is a filtration/drying operation.

22. A compound of formula:

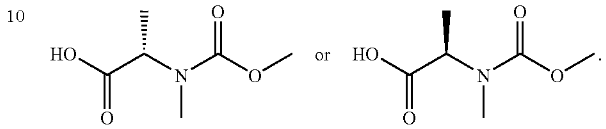

* * * * *